(12) United States Patent
Kiss et al.

(10) Patent No.: US 9,718,744 B2
(45) Date of Patent: *Aug. 1, 2017

(54) HYDROALKYLATING PROCESS COMPRISING AN ACTIVATION OF THE HYDROALKYLATION CATALYST AND METHOD OF MAKING PHENOL AND CYCLOHEXANONE

(71) Applicant: ExxonMobil Chemical Patents Inc., Baytown, TX (US)

(72) Inventors: Gabor Kiss, Hampton, NJ (US); Thomas E. Green, Hamilton, NJ (US); Keith H. Kuechler, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,123

(22) PCT Filed: Sep. 26, 2014

(86) PCT No.: PCT/US2014/057706
§ 371 (c)(1),
(2) Date: Mar. 18, 2016

(87) PCT Pub. No.: WO2015/057374
PCT Pub. Date: Apr. 23, 2015

(65) Prior Publication Data
US 2016/0229767 A1    Aug. 11, 2016

Related U.S. Application Data

(60) Provisional application No. 61/892,650, filed on Oct. 18, 2013.

(30) Foreign Application Priority Data

Jan. 16, 2014    (EP) ..................................... 14151407

(51) Int. Cl.
| | | |
|---|---|---|
| C07C 45/53 | (2006.01) |
| C07C 37/08 | (2006.01) |
| C07C 2/74 | (2006.01) |
| B01J 37/18 | (2006.01) |
| B01J 29/74 | (2006.01) |
| C07C 407/00 | (2006.01) |
| B01J 38/10 | (2006.01) |
| B01J 29/76 | (2006.01) |
| B01J 29/90 | (2006.01) |
| B01J 29/064 | (2006.01) |
| C07C 29/00 | (2006.01) |

(52) U.S. Cl.
CPC ............... *C07C 2/74* (2013.01); *B01J 29/064* (2013.01); *B01J 29/7476* (2013.01); *B01J 29/7676* (2013.01); *B01J 29/90* (2013.01); *B01J 37/18* (2013.01); *B01J 38/10* (2013.01); *C07C 29/00* (2013.01); *C07C 37/08* (2013.01); *C07C 45/53* (2013.01); *C07C 407/00* (2013.01); *B01J 2229/186* (2013.01); *B01J 2229/34* (2013.01); *B01J 2229/42* (2013.01); *C07C 2529/70* (2013.01); *C07C 2529/74* (2013.01); *C07C 2601/14* (2017.05); *Y02P 20/52* (2015.11); *Y02P 20/584* (2015.11)

(58) Field of Classification Search
CPC ............ C07C 45/53; C07C 37/08; C07C 2/74
USPC .......................... 568/342, 347, 798; 585/467
See application file for complete search history.

(56) References Cited

U.S. PATENT DOCUMENTS

| | | | |
|---|---|---|---|
| 3,760,017 | A | 9/1973 | Arkell et al. |
| 3,760,018 | A | 9/1973 | Suggitt et al. |
| 4,268,699 | A | 5/1981 | Murtha et al. |
| 4,329,531 | A | 5/1982 | Murtha et al. |
| 5,053,571 | A | 10/1991 | Makkee |
| 5,449,847 | A | 9/1995 | Chang et al. |
| 6,037,513 | A | 3/2000 | Chang et al. |
| 7,910,778 | B2 | 3/2011 | Chen et al. |
| 9,364,823 | B2 | 6/2016 | Kiss et al. |
| 9,555,403 | B2 | 1/2017 | Kiss et al. |
| 2012/0178969 | A1 | 7/2012 | Cheng et al. |

FOREIGN PATENT DOCUMENTS

| | | |
|---|---|---|
| WO | 01/47840 | 7/2001 |
| WO | 2011/001244 | 1/2011 |
| WO | 2012/050751 | 4/2012 |

OTHER PUBLICATIONS

Slaugh, L. et al. "Hydrodimerization of Benzene to Phenylcyclohexane over Supported Transition Metal Catalysts," Journal of Catalysis, 1969, vol. 13, pp. 385-396.

Ivanova, I.I. et al., "Hydroalkylation of benzene and ethylbenzene over Ru- and Nicontaining zeolite catalysts—novel catalytic route for ethylcyclohexylbenzene synthesis," From Zeolites to Porous MOF Materials—the 40th Anniversary of International Zeolite Conf., Elsevier, 2007. p. 1228-1235.

*Primary Examiner* — Sikarl Witherspoon

(57) ABSTRACT

Disclosed is a hydroalkylation process in which the hydroalkylation catalyst is activated in the presence of a flowing fluid comprising hydrogen and a condensable agent. The presence of the condensable agent enables fast, effective activation of the hydroalkylation catalyst precursor in a cost-effective manner. It also yields superior catalyst performance.

22 Claims, No Drawings

HYDROALKYLATING PROCESS COMPRISING AN ACTIVATION OF THE HYDROALKYLATION CATALYST AND METHOD OF MAKING PHENOL AND CYCLOHEXANONE

PRIORITY CLAIM

This application is a National Stage Application of International Application No. PCT/US2014/057706 filed Sep. 26, 2014, which claims priority to U.S. Provisional Application Ser. No. 61/892,650 filed Oct. 18, 2013, and European Application No. 14151407.5, filed Jan. 16, 2014, the disclosures of which are fully incorporated herein by their reference.

FIELD

The present invention relates to a process for hydroalkylating an aromatic compound. In particular, the present invention relates to a process for hydroalkylating benzene for making cyclohexylbenzene. The present invention is useful, e.g., in making phenol and cyclohexanone via the route of benzene hydroalkylation.

BACKGROUND

Phenol and cyclohexanone are important materials in the chemical industry and are useful in, for example, the production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone. In addition, the cost of propylene feed is generally high.

Thus, a process that uses alternative feeds and coproduces higher-value ketones, such as cyclohexanone, rather than acetone may be an attractive alternative route to the production of phenols.

It is known from, e.g., U.S. Pat. No. 6,037,513 that cyclohexylbenzene can be produced by contacting benzene with hydrogen in the presence of a bifunctional catalyst comprising a molecular sieve of the MCM-22 type and at least one hydrogenation metal selected from Pd, Ru, Ni, Co, and mixtures thereof. This reference also discloses that the resultant cyclohexylbenzene can be oxidized to the corresponding hydroperoxide which is then decomposed to the desired phenol and cyclohexanone co-product.

In the hydroalkylation step, both the conversion of the aromatic compound (e.g., benzene) and the selectivity of the target alkylated aromatic compound are substantially determined by the performance of the hydroalkylation catalyst. It has been found that the activation process of the hydroalkylation catalyst in the presence of hydrogen can affect catalyst performance significantly. Although various activation processes for the hydroalkylation catalyst have been explored and disclosed before, there is still room for improvement in this regard.

SUMMARY

It has now been unexpectedly discovered that activating a hydroalkylation catalyst precursor in the presence of hydrogen gas and a condensable agent comprising a hydrocarbon compound can significantly improve the performance of the hydroalkylation catalyst. The present disclosure is based on this discovery.

Thus, a first aspect of the present disclosure relates to a hydroalkylation process, the process comprising:

(I) providing a catalyst precursor comprising a solid acid and a hydrogenation metal;

(II) treating the catalyst precursor under activation conditions in the presence of hydrogen and a condensable agent comprising a hydrocarbon compound to produce an activated catalyst, wherein the molar ratio of hydrogen to the condensable agent is at least 3.0; and subsequently (III) contacting the activated catalyst with a first aromatic compound and hydrogen under hydroalkylation conditions to produce a hydroalkylation product comprising a alkylated aromatic compound.

A second aspect of the present disclosure relates to a process for making phenol and/or cyclohexanone, the process comprising:

(A) producing cyclohexylbenzene by:
  (AI) supplying hydrogen and benzene into a hydroalkylation reactor;
  (AII) contacting the hydrogen and benzene with a hydroalkylation catalyst produced by a process according to the first aspect of the present disclosure above;
(B) oxidizing at least a portion of the cyclohexylbenzene to obtain an oxidation product comprising cyclohexylbenzene hydroperoxide; and
(C) subjecting at least a portion of the cyclohexylbenzene hydroperoxide in the oxidation product to cleavage to obtain a cleavage product comprising phenol and cyclohexanone.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, the steps in a process may be conducted sequentially in the order as they are listed, with or without overlapping with one or more other step(s), or in any other order, as the case may be. In addition, two or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, steps are performed in the order as listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two or more different types of the hydrogenation metal(s) are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene.

As used herein, the generic term "phenylcyclohexene" includes, in the aggregate, 2-phenyl-1-cyclohexene, 3-phenyl-1-cyclohexene, and 4-phenyl-1-cyclohexene, unless clearly specified to mean only one or two thereof.

The term "MCM-22 type material" (or "material of the MCM-22 type," "molecular sieve of the MCM-22 type," or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

A hydroalkylation process according to the present disclosure may involve a gaseous phase comprising hydrogen, a liquid phase comprising a first aromatic compound subjected to hydroalkylkation, and a hydroalkylation reaction taking place in the presence of a solid phase catalyst.

In the process of the present disclosure, the first aromatic compound supplied to the hydroalkylation reactor may have the following general formula (F-II):

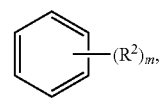

(F-II)

where:

$R^2$, the same or different at each occurrence, each independently represents a substituted or unsubstituted linear, branched acyclic, or cyclic alkyl or alkenyl group having from 1 to 20 carbon atoms (such as 1 to 10, or 1 to 5 carbon atoms); and m is an integer from 0 to 5. Preferably m is 0 or 1.

Non-limiting examples of such aromatic compounds include: benzene, toluene, ethylbenzene, n-propylbenzene, cumene, n-butylbenzene, 2-phenylbutane, o-xylene, m-xylene, p-xylene, o-methylethylbenzene, m-methylethylbenzene, p-methylethylbenzene, and the like.

Thus, a desired product in the reaction effluent of the alkylation process can be an alkylated aromatic compound represented by the following general formula (F-II):

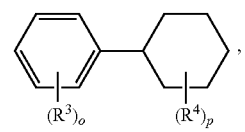

(F-III)

where:

$R^3$ and $R^4$, the same or different at each occurrence, each independently represents a substituted or unsubstituted linear, branched acyclic, or cyclic alkyl or alkenyl having from 1 to 20 carbon atoms (such as from 1 to 10, or from 1 to 5); and o and p are independently integers from 0 to 5. Preferably, o and p are independently 0 or 1.

Non-limiting examples of compounds having formula (F-III) include:
cyclohexylbenzene;
dicyclohexylbenzene;
tricyclohexylbenzene;
methylcyclohexyltoluene;
methylcyclohexyl-ethylbenzene;
ethylcyclohexyl-ethylbenzene;
propylcyclohexyl-propylbenzene;

butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

In hydroalkylation of benzene with hydrogen to produce cyclohexylbenzene, a $H_2$-containing gas feed and a liquid benzene-containing liquid feed may be charged into the hydroalkylation reactor, where the following reactions, among others, may take place on the surface of a bi-functional hydroalkylation catalyst comprising a hydrogenation metal component such as Pd and a solid acid component such as a molecular sieve of the MCM-22 type:

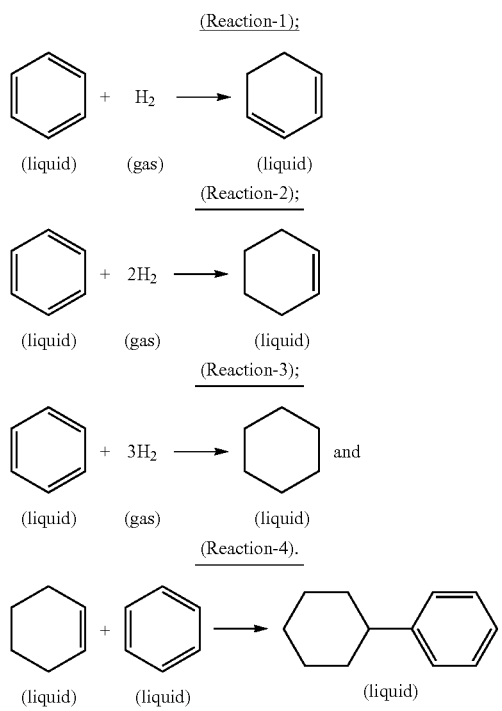

The hydroalkylation catalyst employed in the present process is a bifunctional catalyst comprising an alkylation component such as a solid acid and a hydrogenation metal component, optionally an inorganic oxide support component, and optionally a binder.

Suitable solid acid for the alkylation component include mixed metal oxides, for example, tungstated zirconia, and molecular sieves, for example, zeolite beta, zeolite X, zeolite Y, mordenite and zeolites of the MWW framework type (see "Atlas of Zeolite Framework Types", Fifth edition, 2001). As examples of molecular sieves of the MWW framework type, MCM-22 type molecular sieves described above are particularly advantageous. In one practical example, the molecular sieve of the MWW framework type is MCM-22 or MCM-49.

Any known hydrogenation metal component can be employed as the hydrogenation component in the hydroalkylation catalyst. Particularly advantageous examples include Pd, Pt, Ru, Fe, Rh, Os, Ir, Ni, Zn, Sn, and Co, with Pd and Pt being especially desirable. Thus, the amount of hydrogenation metal component present in the hydroalkylation catalyst may be in a range from Chma1 wt % to Chma2 wt %, based on the total weight of the hydroalkylation catalyst, where Chma1 and Chma2 can be, independently, 0.01, 0.02, 0.03, 0.04, 0.05, 0.06, 0.07, 0.08, 0.09, 0.10, 0.12, 0.15, 0.20, 0.25, 0.30, 0.35, 0.40, 0.45, 0.50, 0.60, 0.70, 0.80, 0.90, 1.0, 2.0, 3.0, 4.0, 5.0, 6.0, 7.0, 8.0, 9.0, or even 10.0, as long as Chma1<Chma2. Where the solid acid component of the catalyst is an aluminosilicate molecular sieve, the molar ratio of the aluminum in the molecular sieve to the hydrogenation metal may be in a range from 1.5 to 1500, for example in a range from 30 to 750, or in a range from 75 to 750, such as in a range from 30 to 300.

The hydrogenation metal may be directly supported on the alkylation component by, for example, impregnation or ion exchange, or can be supported on the inorganic oxide support component, or both. Thus, at least A1 wt % of the hydrogenation metal component may be supported on an inorganic oxide support component separate from but composited with the alkylation component, where the percentage is based on the total weight of the hydroalkylation catalyst, and A1 can be: 50, 55, 60, 75, 80, 85, 90, 95, 98, 99, or even 99.5. By supporting a majority of the hydrogenation metal component on the inorganic oxide support component, the activity of the catalyst and its selectivity to cyclohexylbenzene, dicyclohexylbenzene, and tricyclohexylbenzene in hydroalkylation reaction are increased as compared with an equivalent catalyst in which the hydrogenation metal component is supported directly on the solid acid component.

The inorganic oxide support component contained in such a composite hydroalkylation catalyst is not narrowly defined provided it is stable and inert under the conditions of the hydroalkylation reaction. Suitable inorganic oxides include oxides of elements in Groups 2, 3, 4, 5, 13, and 14 of the Periodic Table of Elements. Examples of suitable and widely available inorganic oxides include, for example, alumina, silica, silica-alumina, titania, zirconia, and combinations and mixtures thereof. As used herein, the numbering scheme for the Periodic Table Groups is as disclosed in Chemical and Engineering News, 63(5), 27 (1985).

Loading the hydrogenation metal component on the inorganic oxide support can be conveniently effected by impregnation of the inorganic oxide support component with a solution of a salt of the desired hydrogenation metal, which can be followed by drying and optional calcination and then compositing with the alkylation component such as solid acid. For example, the catalyst composite can be produced by co-pelletization, in which a mixture of the alkylation component and the metal-containing inorganic oxide support is formed into pellets at high pressure (e.g., from 350 kPa to 350,000 kPa), or by co-extrusion, in which a slurry of the alkylation component and the metal-containing inorganic oxide support, optionally together with a separate binder, which can be organic or inorganic, are forced through a die. Examples of inorganic binder materials are described below. If necessary, additional amount of the hydrogenation metal component can be subsequently deposited on the resultant catalyst composite. Drying can be carried out at a temperature in a range from Td1° C. to Td2° C., where Td1 and Td2 can be, independently, 20, 25, 30, 35, 40, 45, 50, 55, 60, 65, 70, 80, 90, 100, 110, 120, 130, 140, 150, 160, 170, 180, 190, 200, 210, 220, 230, 240, 250, 260, 270, 280, 290, or 300, as long as Td1<Td2. Calcination can be conducted at a temperature in a range from Tc1° C. to Tc2° C., where Tc1 and Tc2 can be, independently, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1000, as long as Tc1<Tc2. Calcination can be conducted advantageously in an atmosphere comprising $O_2$, such as air, so that organic matters contained in the catalyst source materials are burned, reduced or eliminated.

Alternatively, the alkylation component is first extruded with the inorganic oxide component. The thus obtained substrate is dried and optionally calcined, and then the hydrogenation metal is impregnated into the substrate, followed by drying and optional calcination. In this case, the impregnation conditions can be adjusted such that the hydrogenation metal is preferentially associated with the oxide component of the extrudate. Drying and calcination may be conducted as described above.

The hydroalkylation catalyst may further comprise an optional inorganic binder, non-limiting examples of which include clay, silica and/or metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. The binder mechanically connects catalytically active particles comprising the hydrogenation metal, the solid acid, and optionally an inorganic oxide support component into a larger body, such as a pellet, a cylinder, a pill, and the like, which can be convenient loaded into a hydroalkylation reactor.

After the incorporation of the hydrogenation metal component, the alkylation component, optionally the inorganic oxide support component, and optionally the binder, a catalyst precursor of the hydroalkylation catalyst is formed. After calcination, the hydrogenation metal is normally in an inactive oxidized form in the precursor and therefore, before being employed in a hydroalkylation process, the resultant catalyst precursor is desirably activated to convert at least some of the hydrogenation metal content to its zero-valent elemental state. For example, in a Pt-containing catalyst, the Pt would take the form of $PtO_2$ if the precursor has been calcined in the presence of $O_2$. During the activation step, the following Reaction-5 takes place:

$$PtO_2 + 2H_2 \rightarrow Pt + 2H_2O \qquad \text{(Reaction-5)}.$$

The activation process can be conducted by heating the catalyst precursor in the presence of hydrogen in, e.g., the same reactor as that used for the subsequent hydroalkylation step. However, if desired, the activation may be conducted in one or more separate reactors and the activated catalyst is subsequently transferred to the hydroalkylation reactor. Desirably, the activation atmosphere comprises a flowing stream of dry $H_2$-containing gas such that the water produced during the activation reaction above is carried away.

Activation processes for the precursor of hydroalkylation catalysts are described in: co-pending, co-assigned PCT application No. PCT/US2013/049720, filed on Jul. 9, 2013 and entitled "Activation and Use of Hydroalkylation Catalysts;" U.S. Provisional Application Ser. No. 61/712,980, filed on Oct. 12, 2012 and entitled "Activation and Use of Hydroalkylation Catalysts;" and WO2012/050751, the contents of all of which are incorporated herein by reference. While the processes described in these references can acti-vate the precursor of hydroalkylation catalysts, the catalysts thus activated still have room for improvement.

In a surprising manner, it has been discovered that, if the activation of the hydroalkylation catalyst precursor is conducted in the presence of $H_2$ and a condensable agent, the performance of the activated catalyst can be significantly higher than activation in an environment free of the condensable agent. By "condensable agent" is meant an agent having a boiling point higher than 25° C. at 101 kPa pressure. The condensable agent comprises a hydrocarbon, which may have a structure represented by the following formula (F-I):

where:

R', the same or different at each occurrence, each independently represents a substituted or unsubstituted linear, branched acyclic, or cyclic alkyl or alkenyl group having from 1 to 20 carbon atoms; and m is an integer from 0 to 5. Preferably, m is 0 or 1.

The condensable agent may comprise the first aromatic compound of formula (F-II). Non-limiting examples of the compound having formula (F-I) are those examples of the first aromatic compound of formula (F-II) listed above. The condensable agent present in the activating environment can be completely in gaseous phase, or a combination of gaseous and liquid phase. Thus, in the case of benzene hydroalkylation, an example of the condensable agent is benzene.

In the process of the present disclosure, in step (II), the catalyst precursor may be heated in the presence of a flowing stream of gas comprising $H_2$ and a condensable agent. The condensable agent is at least partly present in the flowing stream of gas comprising hydrogen. The condensable agent may also be present in liquid phase directly in contact with the catalyst precursor. The liquid phase is advantageously a flowing stream of material as well. It is highly desired that the fluid(s) (including gas and liquid) directly contacting the catalyst precursor are dry, i.e., comprise water at a concentration of at most 500 ppm, or at most 300 ppm, or even at most 100 ppm, such that water generated during the activation step is effectively purged by the flowing activation stream. The fluid directly contacting the catalyst precursor may advantageously comprise an inert gas, such as $N_2$, $CH_4$, mixtures thereof, and the like.

Without intending to be bound by a particular theory, it is believed that in the process of the present disclosure, by employing a condensable agent in the activation step (II), which has significantly higher heat capacity than $H_2$, the catalyst precursor can be heated to the desired activation temperature more quickly and more uniformly, resulting in better dispersion of the hydrogenation metal in active state on the support. The faster and more uniform heating effect is even more pronounced when a portion of the condensable agent in step (II) is in liquid phase. Traditionally, in a catalyst activation process performed without using a condensable agent, a substantial portion of the activation process is devoted to temperature ramp up before the temperature of the catalyst precursor reaches a desirable, high temperature, e.g., a temperature below the maximum temperature the catalyst precursor is subjected to because, to avoid overheating part of the catalyst precursor while failing to heat other part thereof to the desired high temperature, a slow temperature ramp rate is required. In the process of the present disclosure, one can raise the temperature ramping rate because of the higher heat content of the flowing condensable agent and its high ability to heat the catalyst precursor more uniformly. Furthermore, it was found that the activation process of the present disclosure can be used to achieve high catalyst performance even at low activation temperatures, such as no higher than Ta° C., where Ta can be 300, 280, 260, 250, 240, 220, or even 200. In addition, where the condensable agent reacts exothermically with hydrogen in the presence of the catalyst precursor or partially activated catalyst precursor, such as hydrogenation and/or hydroalkylation (e.g., benzene hydrogenation and hydroalkylation), the heat released from the reaction serves to at least partially provide the heat for raising the temperature of the catalyst precursor to the desired activation temperature. Therefore, the activation process of the present disclosure can significantly reduce (i) the time period required for the temperature ramping period and the total time required for the activation step and/or (ii) the heating capacity and thus the cost of the heating equipment used for heating the activation fluid. Both traits can result in significant cost savings to the hydroalkylation process. Still further, the activation step of the process of the present disclosure enables more even temperature profile in the catalyst bed and it can be easily monitored and controlled as described below resulting in a safe operation.

In the process of the present disclosure, in step (II), the catalyst precursor may be heated to a temperature in a range from T1° C. to T2° C. for a duration of D1 hour(s) to D2 hour(s), where T1 and T2 can be, independently, 100, 110, 120, 130, 140, 150, 160, 170, 180, 190, 200, 210, 220, 230, 240, 250, 260, 270, 280, 290, 300, 320, 340, 350, 360, 380, 400, as long as T1<T2, and D1 and D2 can be, independently, 0.1, 0.2, 0.3, 0.4, 0.5, 0.6, 0.8, 1.0, 1.2, 1.4, 1.5, 1.6, 1.8, 2.0, 3.0, 4.0, 5.0, 6.0, 7.0, 8.0, 9.0, 10, 12, 14, 15, 16, 18, 20, 22, 24, 25, 30, 35, 36, 40, 45, 48. Desirably, T1=120, and T2=350; or more desirably, T1=130, and T2=250.

In the process of the present disclosure, in step (II), the catalyst precursor may be heated by a flowing fluid feed with a maximum temperature of Tmax° C., where Tmax can be any temperature in the range from 120 to 400, e.g., 400, 390, 380, 370, 360, 350, 340, 330, 320, 310, 300, 290, 280, 270, 260, 250, 240, 230, 220, 210, or 200. In specific examples, the catalyst precursor may be treated in the temperature range from (Tmax−20)° C. to Tmax° C. for a total duration in a range from D3 hour(s) to D4 hour(s), where D3 and D4 can be, independently, 0.1, 0.2, 0.3, 0.4, 0.5, 0.6, 0.8, 1.0, 1.2, 1.4, 1.5, 1.6, 1.8, 2.0, 3.0, 4.0, 5.0, 6.0, 7.0, 8.0, 9.0, 10, 12, 14, 15, 16, 18, 20, 22, 24, 25, 30, 35, 36, 40, 45, 48, 50, 54, 60, 66, 72. If Tmax is higher than 400, the catalyst precursor can be harmed resulting in reduced catalyst performance. On the other hand, if Tmax is below 120, the activation process may be too slow and thus the time required to activate the catalyst precursor to the desired level of performance will be too long to be economically viable. Desirably, Tmax is in the range from (Tha−10)° C. to (Tha+100)° C., where Tha is the average temperature of the hydroalkylation process the activated catalyst will be used for.

Based on Tmax, hydroalkylation catalyst activation processes can be sorted into two groups: low- and high-temperature hydroalkylation catalyst activation methods. The Tmax of high-temperature hydroalkylation catalyst activation methods is no less than 250. Desirably, the Tmax of high-temperature hydroalkylation catalyst activation methods is no higher than 350. The Tmax of low-temperature hydroalkylation catalyst activation methods is less than 250. Desirably, the Tmax of low-temperature hydroalkylation catalyst activation methods is no less than 120. Lower activation temperatures are advantageous since they take less time to ramp up to and need less heat and lower activation gas feed temperature to perform catalyst activation. Lower activation temperature requirement thus may also reduce the capital equipment cost needed for startup by requiring smaller, lower temperature furnace. The currently disclosed hydroalkylation catalyst activation processes include both low- and high-temperature catalyst activation methods, though the low-temperature hydroalkylation catalyst activation method is often advantageous.

In step (II) of the process of the present disclosure, the molar ratio of hydrogen to the condensable agent (Rhc) of the fluid the catalyst precursor is exposed to is at least 3.0. Desirably, Rhc is in a range from Rhc1 to Rhc2, where Rhc1 and Rhc2 are, independently, 3.0, 3.1, 3.2, 3.3, 3.4, 3.5, 3.6, 3.7, 3.8, 3.9, 4.0, 4.2, 4.5, 4.8, 5.0, 5.2, 5.5, 5.8, 6.0, 6.5, 7.0, 7.5, 8.0, 8.5, 9.0, 9.5, 10.0, 12.0, 14.0, 15.0, 18.0, 20.0, 25.0, 30.0, 35.0, 40.0, 45.0, 50.0, 80.0, or 1000, as long as Rhc1<Rhc2. In one example, Rhc1=3.0, and Rhc2=20.0. Without intending to be bound by a particular theory, it is believed that if the ratio of $H_2$ to the condensable agent is lower than 3.0, coking can occur on the surface of the catalyst during the activation step, which can result in reduced catalyst activity. Such coking is detrimental to catalysts in general, and especially so for catalyst precursors under activation. High $H_2$ to the condensable agent in the activation fluid such as at least 3.0, or at least 4.0, would significantly reduce the probability of coke produced and its amount, if any at all.

Step (II) also may include heating the catalyst precursor from around room temperature to 100° C. at a temperature elevation (ramp) rate of Ter1° C./hour to Ter2° C./hour, where Ter1 and Ter2 can be, independently, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 12.0, 15.0, 18.0, 20.0, 22.0, 25.0, 28.0, 30.0, 32.0, 35.0, 38.0, 40.0, 42.0, 45.0, 48.0, 50.0, 52.0, 54.0, 55.0, 56.0, 58.0, or 60.0, as long as Ter1<Ter2. Desirably, Ter1=1.0, and Ter2=10.0. Before the catalyst precursor is heated to 100° C., the reduction and thus activation of the hydrogenation metal on the catalyst precursor may occur very slowly. Thus, the pre-treatment of heating the catalyst precursor from, e.g., around room temperature, to 100° C. can be performed at a higher temperature ramp rate than after the catalyst precursor has reached 100° C.

Step (II) may also include heating the catalyst precursor from around room temperature to Tmax° C. at a temperature elevation (ramp) rate of Ter1° C./hour to Ter2° C./hour, where Tmax is defined above, Ter1 and Ter2 can be, independently, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 12.0, 15.0, 18.0, 20.0, 22.0, 25.0, 28.0, 30.0, 32.0, 35.0, 38.0, 40.0, 42.0, 45.0, 48.0, 50.0, 52.0, 54.0, 55.0, 56.0, 58.0, or 60.0, as long as Ter1<Ter2. Desirably, Ter1=1.0, and Ter2=10.0.

In practical commercial embodiments the temperature ramp rate in step (II) described in the preceding paragraphs may be limited by the rate at which heat can be delivered to the catalyst bed, which in packed bed reactors without internal heat exchangers is a function of the combination of feed temperature, flow rate, and heat capacity, the latter of which is a function of feed composition. Practical catalyst bed ramp rates during the activation process of the present disclosure can be on the high end described in the preceding paragraph because of the high heat content of the condensable agent employed in the activation fluid, even though lower temperature ramp rate is feasible if necessary. Higher ramp rates are advantageous because catalyst activation can be performed faster and thus the plant can be put in production faster.

In addition, where the condensable agent can react with $H_2$ in the presence of the catalyst precursor or a partially or completely activated hydroalkylation catalyst, such as a condensable agent having a general formula (F-I) above, the reaction between the condensable agent and $H_2$ can significantly reduce the amount of $H_2$ available for the activation reactions. Further, the reaction products between the condensable agent and $H_2$ can be a coking agent or source thereof. In such case, it is desired that the molar ratio of $H_2$ to the condensable agent in the fluid the catalyst precursor is exposed to is at least sufficient to allow for the complete hydrogenation of the condensable agent, i.e., at least sufficient to convert the condensable agent to a saturated hydrocarbon compound under the activation condition. Thus, for example, where the condensable agent comprises benzene, because one mole of benzene may consume three moles of $H_2$ to form its saturated derivative, cyclohexane, it is highly desired that the $H_2$ to benzene molar ratio in the activating fluid stream the catalyst precursor is exposed to during activation is at least 3, such as at least 3.5, 4.0, 4.5, 5.0, 6.0, 7.0, 8.0, 9.0, 10.0, 12.0, 15.0, 18.0, 20.0, 30.0, 40.0, 50.0, 60.0, 70.0, 80.0, 90.0, 100.0, 150.0, 200.0. Using high $H_2$ to condensable agent molar ratios may reduce the benefits of the process of the present disclosure. For example, if the $H_2$ to the condensable agent molar ratio is above 200.0, the benefit of using the condensable agent may be too small to be meaningful.

Hydroalkylation can be performed in reactors with fixed beds that are effectively adiabatic. The activation step (II) of the process of the present disclosure may be conducted in similar reactors. In an adiabatic fixed bed, the heat released by the partial or full hydrogenation of the condensable agent (such as benzene) may lead to excessive temperatures. This potential for exotherm temperature runaway can be avoided. In the process of the current disclosure this can be accomplished by limiting the condensable agent (such as benzene) inventory in fixed bed reactors by operating them in a down-flow mode during activation. Temperature runaways can be also prevented by monitoring the temperature of the catalyst precursor bed at multiple points and cutting off the benzene feed when the temperature exceeds the target maximum value by 20° C., or by 30° C., or by 40° C., or by 50° C. Stopping the condensable agent (such as benzene) feed stops a major source of the heat supply thus ensuring that the reactor temperature does not rise to unsafe levels.

The pressure applied during activation can be determined by practical operational and investment cost drivers. In the currently disclosed catalyst activation processes the total absolute internal pressure in the reactor can range from Pa1 kPa to Pa2 kPa, where Pa1 and Pa2 can be, independently, 80, 90, 100, 110, 120, 130, 140, 150, 160, 170, 180, 190, 200, 250, 300, 400, 500, 600, 700, 800, 900, 1000, 2000, 3000, 4000, 5000, 6000, 7000, as long as Pa1<Pa2. For economic reasons, the catalyst activation pressure is advantageously not higher than the typical operating pressure of the hydroalkylation process to avoid the requirement and cost for higher pressure rating than what is needed for hydroalkylation process itself. Since hydroalkylation with Pd—$Al_2O_3$/MWW-type zeolite catalysts typically can be performed at good yields and productivity below an absolute pressure of 1750 kPa, the catalyst activation pressure according to the current disclosure is advantageously not higher than 1750 kPa, although higher activation pressures can be applied if so desired without harming catalyst performance.

The flow rate of the activation feed can vary in a wide range without altering the efficiency of the activation process. The selection of feed rate is thus mostly dependent on the desired temperature ramp rate and cost considerations. Expressing it in terms of the hydrogen flow rate (as part of the activation feed also comprising one or more condensable aromatic hydrocarbons), it can be from 10 to 10,000 (volume $H_2$)/(volume catalyst×hour) Gas Hourly Space Velocity (or in short hand 10/hour to 10,000/hour GHSV), or from 10/hour to 5,000/hour, or from 50/hour to 5,000/hour, or from 100/hour to 5,000/hour, or from 50/hour to 3,000/hour, or from 100/hour to 3,000/hour GHSV. Expressing it in terms of the condensable agent feed component flow rate (as part of the activation feed also comprising hydrogen), it can be from 0.01 to 10 (weight condensable aromatic hydrocarbon)/(weight catalyst×hour) Weight Hourly Space Velocity (or in short hand 0.01/hour and 10/hour WHSV), or from 0.1/hour to 10/hour, or from 0.1/hour to 5/hour WHSV.

After heating the catalyst precursor at a desired activation temperature for the desired period of time as described above, the catalyst reaches the desired level of performance, and thus can be cooled down to a desired, lower temperature. If the catalyst precursor is activated in the hydroalkylation reactor in which the activated catalyst is subsequently used, it is desired that the activated catalyst is then cooled down to the use temperature, with the presence of a part or the whole of the activation fluid including hydrogen and the condensable agent. Once the temperature of the activated catalyst reaches the hydroalkylation operation temperature, the hydroalkylation reaction feed can be supplied into the reactor to replace the activation fluid, whereby the hydroalkylation reaction starts. Alternatively, during the cool down period from a high activation temperature, only a stream of hydrogen or other inert or reducing gas can be passed through the catalyst without added amount of the condensable agent.

During the hydroalkylation reaction, in the hydroalkylation reactor, the activated hydroalkylation catalyst is located in a first reaction zone. Thus, the feed materials including the first aromatic compound such as, for example, benzene, and hydrogen, are mixed and allowed to contact the activated hydroalkylation catalyst. Desirably, the feed materials are fed into the hydroalkylation reactor from the top and then flow downward through a bed of the activated hydroalkylation catalyst due to gravity and pressure gradient. On contacting the hydrogenation metal component and alkylation component, the first aromatic compound and hydrogen react to produce a hydroalkylation reaction mixture comprising hydrogen, an alkylated aromatic compound, such as, for example, cyclohexylbenzene in the case of benzene hydroalkylation, and optionally other compounds, such as olefins.

The hydroalkylation reaction mixture may be subjected to additional treatment such as hydrogenation in a downstream second reaction zone of the same hydroalkylation reactor, which is located below the first reaction zone if the first aromatic compound and hydrogen feed(s) are supplied from the top of the hydroalkylation reactor. Such additional treatment may include, e.g., hydrogenation by contacting with a layer of hydrogenation catalyst. The optionally additionally treated hydroalkylation reaction mixture can then exit the hydroalkylation reactor as one or more streams. Where multiple streams exited the hydroalkylation reactor, those streams may have the same or different compositions. For example, one stream may comprise more hydrogen than the other.

It has been found that the molar ratio of hydrogen gas to the first aromatic compound fed into the reactor partly determines the extent to which desired and undesired reactions take place on the catalyst. For example, in the case of hydroalkylation of benzene, where there is a substantial oversupply of $H_2$, more cyclohexane bicyclohexylbenzene may be produced; and in the case of a substantial oversupply of benzene, more biphenyls may be produced. In a hydroalkylation reaction where the target product is cyclohexylbenzene, all by-products cyclohexane, biphenyl, and bicyclohexane are undesired and should be minimized. Therefore, the molar ratio of $H_2$ to benzene is desired to be within a given range in the feed materials, such as from RM1 to RM2, where RM1 can be 0.01, 0.05, 0.10, 0.15, 0.20, 0.25, 0.30, 0.35, 0.40, 0.45, 0.50, 0.60, 0.80, 1.00, and RM2 can be 15.0, 10.0, 8.0, 6.0, 4.0, 2.0, 1.5, 1.0, 0.90, 0.80, 0.70, 0.60, as long as RM1<RM2. Desirably, RM1 is 0.10, and RM2 is 1.5.

It is highly desired that the first aromatic compound fed into the hydroalkylation reactor is in at least partly in liquid state, while hydrogen is supplied into the hydroalkylation reactor as a stream of gas containing hydrogen gas and optionally an inert gas such as methane. The two feed materials may be combined before or immediately after entering the hydroalkylation reactor.

The process according to the present disclosure may be conducted in a fixed-bed catalyst reactor, where the catalyst particles are packed inside a column, and the gas and liquid materials are allowed to travel, e.g., in a direction from the top to bottom, in contact with the surface of the hydroalkylation catalyst particles and the hydrogenation catalyst particles, whereby the hydroalkylation and/or hydrogenation reactions take place.

In the process of the present disclosure, both hydrogen and the first aromatic compound can be fed into the hydroalkylation reactor from a location above the bed of the hydroalkylation catalyst, mix together and travel through the hydroalkylation catalyst bed in an upper first reaction zone, produces a first reaction mixture, which travels downward through a second bed of hydrogenation catalyst and is converted into a second reaction mixture, and the second reaction mixture exits the hydroalkylation reactor at locations in proximity to the bottom of the bed of the hydrogenation catalyst, such as locations below the bottom of the bed of the catalyst. This down-flow configuration is particularly advantageous for carrying out gas-liquid reaction on the surface of a solid catalyst bed and can allow for a substantially uniform distribution of both liquid and gas in a horizontal cross-section of the solid catalysts. In such reactors, the liquid is first dispensed onto the upper surface of the hydroalkylation catalyst, then flows down the bed along the boundary of the catalyst particles, wet the surface of the catalyst particles in the bed along its way, and undergoes the desired reaction(s). A substantially uniform distribution of the liquid reaction media inside the bed of the catalyst is highly desired to control the amount of by-products produced inside the reactor. It was found that the distribution of the liquid fed into the reactor to the upper surface of the bed of the catalyst can significantly impact the distribution of the liquid reaction medium in the bulk of the bed of the catalyst. To achieve a substantially uniform distribution of the liquid reaction medium in the bulk, it is highly desired that the liquid fed into the reactor is distributed substantially uniformly to the upper surface of the bed.

In the processes of the present disclosure, at least a portion of both of hydrogen and the first aromatic compound can be fed into the hydroalkylation reactor are supplied to the reactor at the same horizontal level of the reactor. Hydrogen and the first aromatic compound may be mixed and then fed into the hydroalkylation reactor together via the same port(s). Alternatively, hydrogen and the first aromatic compound are fed into the reactor via different, separate ports. At least some of the ports through each of which hydrogen and/or the first aromatic compound are fed into the reactor are above the upper surface of the bed of the hydroalkylation catalyst. To facilitate a substantially uniform distribution of the liquid aromatic compound feed material to the upper surface of the bed of the hydroalkylation catalyst, a plurality of ports may be used above the upper surface of the hydroalkylation catalyst bed, through each of which a portion of the total liquid feed is delivered into the reactor. Generally, it is easier to achieve a substantially uniform distribution of the hydrogen gas in the space above the upper surface of the bed of the hydroalkylation catalyst than the liquid aromatic compound feed material. Nonetheless, to ensure such uniform distribution of hydrogen gas, multiple ports for feeding gas may be used above the upper surface of the bed of the hydroalkylation catalyst as well.

It has been found that, in order to achieve a substantially uniform distribution of the liquid feed material in the space immediately above the upper surface of the bed of the catalyst, a fluid distributing device may be desired between the inlet of the liquid and the upper surface of the bed of the catalyst. Such fluid distributing device receives the liquid material fed into the reactor through the inlet(s), redirects the flow thereof in multiple horizontal directions, and eventually delivers the liquid into the space above the upper surface of the bed in the form of liquid droplets. Detailed description of fluid distributing devices suitable for the process of the present disclosure can be found in co-pending, co-assigned U.S. provisional patent application Ser. No. 61/736,581, filed on Dec. 13, 2012 and entitled "Alkylating Process," the content of which is incorporated herein by reference in its entirety. The temperature inside the hydroalkylation reactor can be monitored by using one or more temperature sensors. To control the temperature inside the reactor, the feed can be adjusted by increasing or reducing the amount of the first aromatic and/or hydrogen supplied. Advantageously, the amount of the first aromatic compound can be changed to quickly control the amount of heat generated from the hydrogenation reaction(s) and alkylation reaction(s).

The present invention can be advantageously employed in the process for making phenol and/or cyclohexanone via benzene hydroalkylation. Detailed description of the process is provided as follows.

Production of Cyclohexylbenzene

In the integrated process for producing phenol and cyclohexanone from benzene, the benzene can be initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-5 to produce cyclohexylbenzene (CHB) according to a process of the present disclosure:

(Reaction-5).

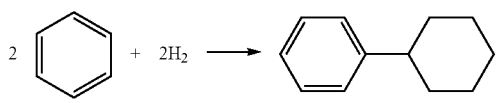

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

Although the benzene hydroalkylation reaction is highly selective towards cyclohexylbenzene, the effluent from the hydroalkylation reaction may contain some dialkylated products, unreacted benzene and cyclohexane. The unreacted benzene may be recovered by distillation and recycled to the reactor. The lower effluent from the benzene distillation may be further distilled to separate the monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene produced in the hydroalkylation step is fed to an oxidizing step, which can be conducted in one or more oxidation reactor(s). Desirably, at least a portion of the cyclohexylbenzene contained in the oxidation feed is converted to cyclohexyl-1-phenyl-1-hydroperoxide, the desired hydroperoxide according to the following Reaction-6:

(Reaction-6).

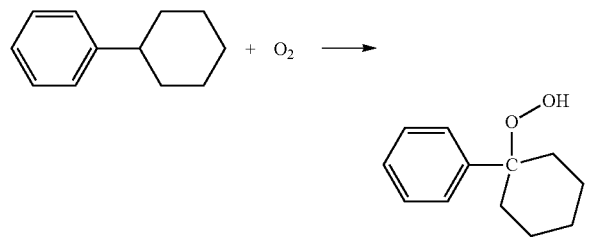

A feed supplied to the oxidizing step may comprise cyclohexylbenzene at a concentration in a range from C1 wt % to C2 wt %, based on the total weight of the feed introduced into the oxidation reactor, where C1 and C2 can be, independently, 10, 20, 30, 40, 50, 60, 70, 80, 90, 92, 94, 95, 96, 97, 98, 99, 99.5, or even 99.9, or even higher, as long as C1<C2. In addition, the feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) phenol at a concentration no greater than 1000 ppm, such as no greater than 100 ppm; and (v) olefins or alkene benzenes such as phenylcyclohexene at no greater than 1000 ppm (or no greater than 800, 600, 500, 400, 300, 200, 100, 80, 60, 50, 40, 20, 10, 8, 6, 5, 4, 2, 1 ppm), which is advantageously reduced by using the process of the present disclosure.

The oxidizing step may be accomplished by contacting an oxygen-containing gas, such as air and various derivatives of air, with the feed comprising cyclohexylbenzene. For example, a stream of pure O$_2$, air, or other O$_2$-containing mixtures may be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

(FC-1)

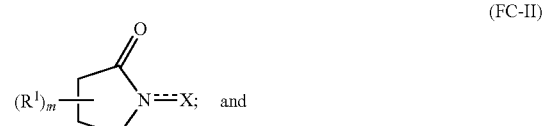
(FC-II)

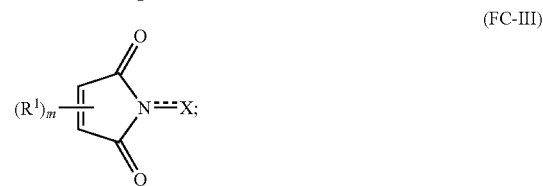
(FC-III)

where:

A represents a ring optionally comprising a nitrogen, sulfur, or oxygen in the ring structure, and optionally substituted by an alkyl group, an alkenyl group, a halogen, or a N—, S—, or O-containing group or other group;

X represents a hydrogen, an oxygen, a hydroxyl group, or a halogen;

R$^1$, the same or different at each occurrence, independently represents a halogen, a N—, S—, or O-containing group, or a linear or branched acyclic alkyl or cyclic alkyl group having 1 to 20 carbon atoms, optionally substituted by an alkyl, an alkenyl, a halogen, or a N—, S—, or O-containing group or other group; and m is 0, 1 or 2.

Examples of particularly suitable catalysts for the oxidation step include those represented by the following formula (FC-IV):

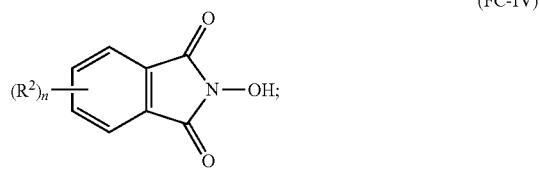

where:

R², the same or different at each occurrence, independently represents a halogen, a N—, S—, or O-containing group, or a linear or branched acyclic alkyl or cyclic alkyl group having 1 to 20 carbon atoms, optionally substituted by an alkyl group, an alkenyl group, a halogen, a S—, O—, or N-containing group, or any other group; and n is 0, 1, 2, 3, or 4.

Especially suitable catalyst having the above formula (FC-IV) for the oxidation step is NHPI (N-hydroxy phthalic imide). Other suitable catalysts are described in U.S. Pat. No. 6,720,462, which is incorporated herein by reference. Specific, non-limiting examples of other suitable catalysts include: 4-amino-N-hydroxyphthalimide; 3-amino-N-hydroxyphthalimide, tetrabromo-N-hydroxyphthalimide; tetrachloro-N-hydroxyphthalimide; N-hydroxyhetimide; N-hydroxyhimimide; N-hydroxytrimellitimide; N-hydroxybenzene-1,2,4-tricarboximide; N,N'-dihydroxy(pyromellitic diimide); N,N'-dihydroxy(benzophenone-3,3',4,4'-tetracarboxylic diimide); N-hydroxymaleimide; pyridine-2,3-dicarboximide; N-hydroxysuccinimide; N-hydroxy(tartaric imide); N-hydroxy-5-norbornene-2,3-dicarboximide; exo-N-hydroxy-7-oxabicyclo[2.2.1]hept-5-ene-2,3-dicarboximide; N-hydroxy-cis-cyclohexane-1,2-dicarboximide; N-hydroxy-cis-4-cyclohexene-1,2 dicarboximide; N-hydroxynaphthalimide sodium salt; N-hydroxy-o-benzenedisulphonimide; and N,N',N"-trihydroxyisocyanuric acid.

Non-limiting examples of suitable reaction conditions of the oxidizing step include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Treatment of the Oxidation Product Before Cleavage

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. The oxidation product may further comprise (i) an oxidation catalyst described above; and (ii) unreacted cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to the oxidizing step, such as cyclohexyl-2-phenyl-1-hydroperoxide, and cyclohexyl-3-phenyl-1-hydroperoxide. These undesired hydroperoxides are desirably at a total concentration of at most 5 wt %, such as at most 3 wt %, 2 wt %, 1 wt %, or even 0.1 wt %.

The oxidation product contains the oxidation catalyst, such as NHPI, and certain by-products. Thus, it may be desirable to wash the oxidation product to remove the by-products and/or the catalyst before cleavage by using an aqueous dispersion. For example, a basic aqueous dispersion, such as a solution of one or more of alkali or alkali earth carbonates, alkali or alkali earth bicarbonates, alkali or alkali earth hydroxides, ammonium hydroxide, may be used to wash the oxidation product to extract NHPI or other similar imide-based catalysts from the oxidation product. In so doing, water concentration in the oxidation product thus washed will increase.

Alternatively, to reclaim the oxidation catalyst from the oxidation product, the oxidation product may be subjected to contacting with a solid sorbent in the form of particles in a slurry or a fixed bed, such as solid alkali or alkali earth metal carbonates, alkali or alkali earth metal bicarbonates, alkali or alkali earth metal hydroxide, molecular sieves, activated carbon, and the like. After separation, the sorbent may be washed using a polar solvent, such as water, acetone, an alcohol, and the like, to reclaim the oxidation catalyst, which can be purified and recycled to the oxidation reactor.

In the process of the present disclosure, at least a portion of the cyclohexylbenzene hydroperoxide in the oxidation product is subjected to a cleavage reaction, desirably in the presence of a catalyst such as an acid, whereby it is converted into phenol and/or cyclohexanone.

At least a portion of the oxidation product may be fed into the cleavage reactor without substantial alteration of the concentration of cyclohexylbenzene hydroperoxide and/or cyclohexylbenzene therein. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: (CCHB(op)−CCHB(cf))/CCHB(cf))<0.05. Thus, the oxidation product may be flashed in a vessel at an absolute pressure in a range from Pf1 kPa to Pf2 kPa to remove a portion of water contained therein, where Pf1 and Pf2 can be, independently, 2.50, 2.67, 3.00, 3.50, 4.00, 4.50, 5.00, 5.50, 6.00, 6.50, 6.67, 7.00, 7.50, 8.00, 8.50, 9.00, 10.00, 11.00, 12.00, 13.00, 13.33, 14.00, 15.00, 16.00, 17.00, 18.00, 19.00, 20.00, 25.00, 30.00, 35.00, 40.00, 45.00, or 50.00, as long as Pf1<Pf2. Desirably, the oxidation product may be flashed in a vessel, such as a flashing drum, at an absolute pressure in a range from 6.67 kPa (50 torr) to 13.33 kPa (100 torr). During the flashing step, other low boiling components that may be present in the oxidation product, such as lower acids (e.g., formic acid, acetic acid, and the like) and low boiling point hydrocarbons (e.g., benzene, cyclohexane, methylcyclopentane, and the like), may be at least partially removed along with water, resulting in a cleaner cleavage feed.

Desirably, at least a portion of the oxidation product is not fed into the cleavage reactor before the concentration of cyclohexylbenzene therein is significantly reduced, and hence, the concentration of cyclohexylbenzene hydroperoxide is significantly increased. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: R1<(CCHB(op)−CCHB(cf))/CCHB(op))≤R2, where R1 and R2 are, independently, 0.05, 0.08, 0.10, 0.12, 0.14, 0.15, 0.18, 0.20, 0.25, 0.30, 0.35, 0.40, 0.45, 0.50, 0.55, 0.60, 0.70, 0.75, 0.80, 0.85, or even 0.90, as long as R1<R2. Desirably, R1=0.25, and R2=0.75. The reduction of cyclohexylbenzene concentration from the oxidation product before cleavage is particularly advantageous where liquid acid, such as sulfuric acid, is used as the cleavage catalyst. Without intending to be bound by a particular theory, it is believed that this is because the liquid acid tends to have low solubility in cyclohexylbenzene, and the desired catalytic effect of the liquid acid can be significantly reduced as a result of high cyclohexylbenzene concentration. Experimental data have shown that partial removal of cyclohexylbenzene concentration from the oxidation product before it is fed to the cleavage step can significantly improve the selectivity of the cleavage reaction to form the desired products, i.e., cyclohexanone and/or phenol.

Because cyclohexylbenzene hydroperoxide is prone to decomposition at an elevated temperature, e.g., at above 150° C., the removal of cyclohexylbenzene from the oxidation product should generally be conducted at a relatively low temperature, e.g., no higher than 150° C., or no higher than 140° C., or no higher than 130° C., or no higher than 120° C., or even no higher than 110° C. Cyclohexylbenzene has a high boiling point (239° C. at 101 kPa). Thus, at the acceptable cyclohexylbenzene-removal temperature, cyclohexylbenzene tends to have very low vapor pressure. Accordingly, to effectively remove a meaningful amount of cyclohexylbenzene from the oxidation product, the oxidation product may be subjected to a very low absolute pressure, e.g., in a range from Pc1 kPa to Pc2 kPa, where Pc1 and Pc2 can be, independently, 0.13, 0.15, 0.20, 0.25, 0.26, 0.30, 0.35, 0.39, 0.40, 0.45, 0.50, 0.60, 0.65, 0.70, 0.75, 0.80, 0.85, 0.90, 0.95, 1.00, 1.33, 1.50, 2.00, 2.50, 2.66, as long as Pc1<Pc2. Desirably, Pc1=0.27, and Pc2=2.00.

Where cyclohexylbenzene is partly removed from the oxidation product before cleavage, water contained in the oxidation product can be at least partly removed at the same time and in the same vessel where the cyclohexylbenzene is partly removed at a low absolute internal pressure.

Because of the very low absolute pressure required for effective cyclohexylbenzene removal, it is highly desired that before the oxidation product is subjected to cyclohexylbenzene removal, components with boiling points substantially lower than cyclohexylbenzene, such as water, benzene, cyclohexane, lower acids, and the like, contained in the oxidation product are removed at a relatively high pressure before the mixture is subjected to the very low pressure required for cyclohexylbenzene removal, such that the vacuum pump used for imparting the very low pressure is not overwhelmed. To that end, the oxidation product, upon exiting the oxidation reactor, may be first flashed in a first vessel such as a flashing drum at an absolute pressure in a range from Pf1 kPa to Pf2 kPa, where Pf1 and Pf2 can be, independently, 2.67, 3.00, 3.50, 4.00, 4.50, 5.00, 6.00, 7.00, 8.00, 9.00, 10.00, 11.00, 12.00, 13.00, 13.33, 14.00, 15.00, 20.00, 25.00, 30.00, 35.00, 40.00, 45.00, 50.00, as long as Pf1<Pf2, where a majority of the water contained in the oxidation product is removed, and desirably less than AA wt % of the cyclohexylbenzene contained in the oxidation product is removed, the percentage based on the total amount of cyclohexylbenzene contained in the oxidation product, where AA can be: 5, 4, 3, 2, 1, 0.8, 0.6, 0.5, 0.4, 0.3, 0.2, or 0.1.

Removal of cyclohexylbenzene from the oxidation product can be advantageously conducted in a concentrator comprising one or more falling film evaporator(s), such as those descried in co-pending, co-assigned U.S. provisional patent application Ser. No. 61/841,072 filed on Jun. 28, 2013 and entitled "Process for Concentrating a Mixture Containing Organic Hydroperoxide." The concentrator advantageously employs one or more falling film evaporators operating in parallel and/or in series operating under very low absolute pressure(s) described above. Because cyclohexylbenzene has a lower boiling point than cyclohexylbenzene hydroperoxide, a portion of the cyclohexylbenzene contained in the oxidation product evaporates under the very low pressure and is enriched in the vapor phase, condensed and collected for recycling back to the oxidizing step. Since by-products produced in the oxidizing step tend to accumulate in the condensed cyclohexylbenzene stream, a washing or extracting treatment of the condensed cyclohexylbenzene using an aqueous dispersion or other agent may be desired before the recycling thereof to the oxidizing step in order to prevent interference of the oxidation reaction of cyclohexylbenzene by the accumulated oxidation by-products. Such aqueous dispersion may be acidic, basic, or neutral in pH. The washing or extracting treatment may advantageously include a first step of chemical wash followed by a step of washing using water only. The thus washed reclaimed cyclohexylbenzene may be dried by using a water sorbent, such as, for example, a 3 Å molecular sieve before being recycled to oxidizing step. Alternatively, because water up to a certain amount is tolerated in the oxidation reactor, the thus washed cyclohexylbenzene, which contains a significant amount of water, may be fed to the oxidizing step directly without drying as at least a portion of the total feed, thus eliminating the cost of drying.

As an alternative approach, water removal of the optionally treated oxidation product can be effected by passing the liquid mixture through a water sorbent, such as a 3 Å molecular sieve. Desirably, the water sorbent also adsorbs the oxidation catalyst, which may be reclaimed by washing with a polar solvent.

Additionally or alternatively, after water removal and before or after partial cyclohexylbenzene removal, all or a portion of the oxidation product may be cooled to cause crystallization of the unreacted imide oxidation catalyst, which may then be separated either by filtration or by scraping from a heat exchanger surface used to effect the crystallization.

Cleavage Reaction

As discussed above, the process for making phenol and cyclohexanone from benzene includes cleaving at least a portion of the cyclohexylbenzene hydroperoxide contained in the oxidation product in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide desirably decomposes in high selectivity to cyclohexanone and phenol, and further, other hydroperoxides present may decompose to form various products, discussed below.

The acid catalyst may be at least partially soluble in the cleavage reaction mixture, stable at a temperature of at least 185° C. and has a lower volatility (higher normal boiling point) than cyclohexylbenzene.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

The cleavage reaction may be conducted under cleavage conditions including a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Thus, the cleavage reaction mixture may contain the acid catalyst at a concentration in a range from Cac1 ppm to Cac2 ppm by weight of the total weight of the cleavage reaction mixture, where Cac1 and Cac2 can be, independently, 1, 2, 3, 4, 5, 6, 7, 8, 9, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Desirably, Cac1 is 10, and Cac2 is 200.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation product undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-12:

(Reaction-12).

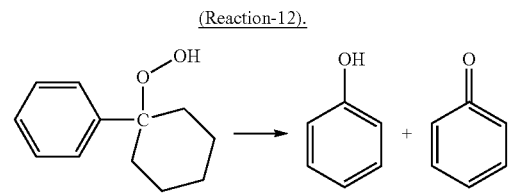

Desirably, each mole of cyclohexyl-1-phenyl-1-hydroperoxide produces one mole of phenol and one mole of cyclohexanone. However, due to side reactions, the selectivity of the cleavage reaction of phenol can range from Sph1% to Sph2% and the selectivity of cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage reaction effluent, or from a downstream separation step. Thus, the cleavage reaction mixture inside the cleavage reactor may comprise, based on the total weight of the cleavage reaction mixture: (i) phenol at a concentration from Cph1 wt % to Cph2 wt %, where Cph1 and Cph2 can be, independently, 20, 25, 30, 35, 40, 45, 50, 55, 60, 65, 70, 75, or 80, as long as Cph1<Cph2; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb1 wt % to Cchb2 wt %, where Cchb1 and Cchb2 can be, independently, 5, 8, 9, 10, 12, 14, 15, 18, 20, 22, 24, 25, 26, 28, 30, 35, 40, 45, 50, 55, 60, 65, 70, as long as Cchb1<Cchb2.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. For example, the cleavage reactor can be a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. For example, cooling coils operating within the cleavage reactor(s) remove at least a portion of heat generated.

The cleavage reaction product exiting cleavage reactor may comprise, based on the total weight of the cleavage reaction mixture: (i) phenol at a concentration from $Cph3$ wt % to $Cph4$ wt %, where $Cph1$ and $Cph2$ can be, independently, 20, 25, 30, 35, 40, 45, 50, 55, 60, 65, 70, 75, or 80, as long as $Cph3<Cph4$; (ii) cyclohexanone at a concentration from $Cch3$ wt % to $Cch4$ wt %, where $Cch3$ and $Cch4$ can be, independently, 20, 25, 30, 35, 40, 45, 50, 55, 60, 65, 70, 75, or 80, as long as $Cch3<Cch4$; (iii) cyclohexylbenzene at a concentration from $Cchb3$ wt % to $Cchb4$ wt %, where $Cchb3$ and $Cchb4$ can be, independently, 5, 8, 9, 10, 12, 14, 15, 18, 20, 22, 24, 25, 26, 28, 30, 35, 40, 45, 50, 55, 60, 65, 70, as long as $Cchb3<Cchb4$.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

The cyclohexylbenzene contained in the cleavage reaction product can be separated from other major components, such as phenol and cyclohexanone by, e.g., distillation. The separated cyclohexylbenzene can then be treated and/or purified, e.g., by washing using an aqueous dispersion, before being delivered to the oxidation step along with cyclohexylbenzene supplied from other resources, such as fresh cyclohexylbenzene produced from the hydroalkylation reactor and a recycle cyclohexylbenzene stream from the cyclohexylbenzene hydroperoxide concentrator.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

EXAMPLES

Reactor setup and catalyst loading employed in the examples of the current disclosure is provided as follows.

Catalyst activation and the hydroalkylation performance tests with the resulting activated catalyst samples were performed in down-flow 0.5" diameter stainless steel fixed bed reactors that were equipped with three-point thermocouples positioned at the center of the reactors. The 4.5" (11.43 cm) long catalyst beds were positioned to ensure that the three thermocouples (placed 2" (5.08 cm) apart) measured the temperatures at the inlet, outlet, and the center of the catalyst beds. In order to reduce the volumetric heat release and thus to afford more isothermal operations, the catalysts were diluted with quartz sand. The diluent also enhanced the even distribution of the activation feed and the hydroalkylation reactants in the catalyst bed. Neat quartz sand was used at either side of the catalyst bed. It served to preheat and evenly distribute the feed at the feed inlet side and to hold the catalyst bed at the exit side, the latter of which was at the bottom of the reactor (down-flow).

The reactors were encased in a 6" (15.24 cm) long 1" (2.54 cm) diameter brass sleeve that were centered along the catalyst beds to improve their temperature control. In the brass sleeves, there were three thermocouples positioned at the two ends and the center of the catalyst beds. The reactors were heated by three-zone clam-shell electrical furnaces. During steady-state operations, the temperatures of the three furnace zones were controlled by utilizing the feedback from the three thermocouples in the brass sleeves of the reactors. The catalyst bed temperatures at the three thermocouples were typically within 2° C. of the set values. The reported reaction temperatures (Trxn) were calculated as the weighted average of the three thermocouple measurements (Tinlet, Tmiddle, Toutlet) by the following formula:

$$Trxn=(Tinlet+2Tmiddle+Toutlet)/4.$$

The catalysts in all experiments nominally consisted of 0.15 wt % Pd supported on alumina-bound MCM-49 (alumina/MCM-49 of 20/80 wt/wt). The catalysts were received in their calcined forms as 1/20" (1.27 mm) extrudates and were stored in closed plastic bottles. Before charging them into the reactors, the catalyst extrudates were broken up and sized to a length/diameter (L/D) ratio of near one (14-20 mesh) to provide reactor beds with proper hydrodynamics. As mentioned above, the catalysts were also diluted with quartz sand that on one hand reduced volumetric catalyst charge and thus volumetric heat release while also improving the desired plug-flow characteristics of the reactant streams passing through the catalyst beds.

In a typical test, 1.8-2.0 grams of 14-20 mesh catalyst diluted with 6 grams quartz was charged into the reactor. After pressure testing, the catalysts were activated by either comparative or inventive activation methods. The former tests were performed with pure, dry hydrogen, while the latter involved co-feeding benzene (as an example for the condensable agent) with hydrogen. The activation tests demonstrating the comparative high-temperature dry activation without a condensable agent (called "dry activation" herein) were performed at 50 psig (345 kPa gauge pressure; 446 kPa absolute pressure), while the treatments according to the currently disclosed activation process were performed at 165 psig (1138 kPa gauge pressure; 1239 kPa absolute pressure). In both cases, the reactor temperature was ramped up to 240° C. value at 5° C./hour ramp rate then holding it there for 2-3 hour. The comparative dry activation method was also performed by ramping the temperature to 300° C. at various ramp rates, most often at 60° C./hour. The nominal $H_2$/benzene ratio in the tests according to the current disclosure was 4 mol/mol. The activation was finished by letting the catalyst cool down to near the hydroalkylation temperature (145° C.) while keeping the pressure and feed flow rates unchanged. The catalyst then was brought on a hydroalkylation stream by adjusting the pressure (in the case of the comparative dry activation test) and the flow rates of benzene and hydrogen to their initial hydroalkylation test values: 165 psig (1138 kPa gauge pressure; 1239 kPa absolute pressure), 0.7 mol/mol $H_2$/benzene, and 2.5/hour benzene WHSV. Occasionally catalyst activity was so high that the reaction became $H_2$ limited. In such instances the hydroalkylation feed rate was adjusted to bring down the conversion to values that allowed ready and meaningful comparisons of the catalyst performances obtained after the various activation processes.

After letting the reactors line out for about 6 hours, the product effluents were periodically directed to chilled knock out vessels held at −5° C. and liquid samples were collected then analyzed by a gas chromatograph equipped with a flame-ionization detector (FID). The response factors for the various product components were determined either by using blends of authentic samples or by using factors published in the J. of Gas Chromatography in February 1967, p 68 by W. A. Dietz. Calibrations were checked by analyzing gravimetrically prepared calibration blends. Benzene conversion and product selectivity were determined from the normalized FID areas by applying the calibration response factors.

The following abbreviations are used in the present disclosure, including the drawings, tables, and the texts of the specification:
  TOS: time on stream
  CHB: cyclohexylbenzene,
  C18: 18-carbon fraction, primarily comprising dicyclohexylbenzene,
  Chex: cyclohexane
  WHSV: weight hourly space velocity expressed as (weight of material)/(weight of catalyst times time in hour)

Example 1 (Comparative): Dry Activation at 300° C.

Three experiments (RN-1A, RN-1B, and RN-2A) were carried out to establish catalyst performance using the comparative high-temperature dry activation process. The catalyst in all three experiments were treated in 50 psig (345 kPa gauge pressure; 446 kPa absolute pressure) pure $H_2$. The $H_2$ flow rates were similar, corresponding to 1988/hour, 1988/hour, and 2305/hour GHSV, respectively. The catalyst bed in each test was ramped up to 300° C. (nominal) at 60° C./hour (nominal) ramp rate and was held at 300° C. for 2 hours. The reactor then was cooled to the hydroalkylation temperature (145° C.). After the reactor was cooled near the desired temperature, it was brought on hydroalkylation stream at 145° C., 165 psig total pressure (1138 kPa gauge pressure; 1239 kPa absolute pressure), 0.7 mol/mol $H_2$/benzene feed, 2.5/hour or 3.4/hour benzene WHSV. Interestingly, benzene conversion gradually increased indicating an increasing catalyst activity in all three tests at the start of the run. In fact, in RN-1A and RN-1B, benzene conversion at the initial 2.5/hour benzene WHSV increased over time to nearly 50% causing high $H_2$ conversion. Thus, to avoid $H_2$ depletion in the reactor, benzene WHSV was increased to 3.4/hour WHSV in these two runs. Seeing this activity increase, the third run, RN-2A, was started at the higher, 3.4/hour benzene WHSV. Benzene conversion (catalyst activity) peaked after about 310 hours on stream, then somewhat declined. To test the effect of another high-temperature hydrogen treatment, the catalyst was rejuvenated in RN-1B after 387 hours on hydroalkylation stream. This rejuvenation entailed first turning off the benzene feed and reducing the pressure to about 13 psig (90 kPa gauge pressure; 191 kPa absolute pressure) and increasing the $H_2$ flow rate to 2353/hour GHSV to flash off the liquids in the catalyst bed for about two hours. After this drying, the pressure was raised to 50 psig (345 kPa gauge pressure; 446 kPa absolute pressure) and the $H_2$ flow was adjusted to 1988/hour GHSV as was used in the initial activation procedure. The rest of the rejuvenation protocol followed the initial catalyst treatment (nominally 60° C./hour ramp to 300° C., hold for 2 hours, cool in $H_2$ and then bring catalyst back to hydroalkylation stream and conditions). TABLE 1 below lists benzene conversion and product selectivity at the start of run (around 20 hours time on hydroalkylation stream), at the peak catalyst activity (around 310 hours on stream), and after about another 350 hours on stream as the catalyst passed its peak activity and was approaching a lined out condition characterized by a slow loss of catalyst activity. For RN-1B, the results are also listed after rejuvenation as the catalyst was brought back on stream. After rejuvenation, the catalyst reached peak activity at around 550 hours on hydroalkylation stream or about 160 hours on stream after rejuvenation.

TABLE 1

Performance of catalyst after 300° C. (high-temperature) dry activation

| Run # RN- | TOS (hour) | Benzene WHSV (1/hour) | Benzene Conversion (%) | Product Selectivity | | |
|---|---|---|---|---|---|---|
| | | | | CHB (%) | C18 (%) | Chex (%) |
| 1A | 20 | 2.5 | 35.0 | 73.4 | 12.8 | 11.8 |
| 1B | 20 | 2.5 | 34.1 | 73.3 | 12.3 | 12.2 |
| 2A | 21 | 3.4 | 24.1 | 75.2 | 10.6 | 11.6 |
| 1A | 311 | 2.5 | 48.6 | 71.5 | 16.7 | 9.6 |
| 1B | 313 | 2.5 | 48.3 | 70.9 | 16.7 | 10.2 |
| 2A | 315 | 3.4 | 38.3 | 74.8 | 14.7 | 8.5 |

TABLE 1-continued

Performance of catalyst after 300° C. (high-temperature) dry activation

| Run # RN- | TOS (hour) | WHSV (1/hour) | Benzene Conversion (%) | CHB (%) | C18 (%) | Chex (%) |
|---|---|---|---|---|---|---|
| 1A | 383 | 3.4 | 37.2 | 74.6 | 15.1 | 8.4 |
| 1B | 383 | 3.4 | 38.4 | 73.1 | 15.7 | 9.4 |
| 2A | 427 | 3.4 | 37.7 | 74.9 | 14.5 | 8.3 |
| 1B | 433 | 3.4 | 38.7 | 71.6 | 17.3 | 8.7 |
| 1B | 550 | 3.4 | 44.8 | 68.9 | 19.7 | 8.9 |
| 1A | 673 | 3.4 | 35.0 | 75.6 | 14.8 | 7.5 |
| 1B | 670 | 3.4 | 41.4 | 71.3 | 17.2 | 9.2 |
| 2A | 669 | 3.4 | 35.6 | 75.7 | 14.2 | 7.3 |

A comparison of the results obtained up to 383/427 hours on hydroalkylation stream shows that although catalyst activity evolves with time on stream, the results are reproducible as all three runs yielded benzene conversion and selectivity values within typical experimental scatter. Comparing the results of RN-1B and the two other runs, RN-1A and -2A, at around 670 hours on hydroalkylation stream, it is clear that the second high-temperature hydrogen treatment (rejuvenation) in RN-1B increased catalytic activity (see benzene conversion of 41.4% in RN-1B vs. 35.0-35.6% in RN-1A and 2A at around 670 hours on stream). The expected selectivity shift towards heavier (C18) hydroalkylation products at the expense of CHB at higher benzene conversion can also be observed. Finally, it is worth pointing out that the initial cyclohexane selectivity is always higher than what is obtained after the catalyst ages for a few days. It is also somewhat higher at higher benzene conversions, which adds to the CHB selectivity loss caused by the earlier mentioned higher C18 make. Finally, note that CHB selectivity of the lined out catalyst (around 670 hours on stream) is 76% at 35% benzene conversion.

Example 2 (Comparative): Low-Temperature Dry Activation Process

WO2012/050751 discloses a low-temperature dry hydroalkylation catalyst activation method. Here we now incorporate the results from two experiments RN-3A and RN-4A using that method. The catalysts were activated in flowing $H_2$ at 50 psig (345 kPa gauge pressure; 446 kPa absolute pressure) by ramping the temperature from ambient to 240° C. at 5° C./hour then holding the temperature at nominally 240° C. for 2 hours. The $H_2$ flow rates corresponded to 118/hour and 136/hour GHSV, respectively. The results are summarized below in analogous fashion as shown in Example 1 above in TABLE 2.

TABLE 2

Performance of catalyst after 240° C. (low-temperature) dry activation

| Run # RN- | TOS (hour) | WHSV (1/hour) | Benzene Conversion (%) | CHB (%) | C18 (%) | Chex (%) |
|---|---|---|---|---|---|---|
| 3A | 44 | 3.4 | 28.1 | 77.7 | 11.8 | 8.4 |
| 4A | 45 | 3.5 | 27.5 | 78.1 | 11.1 | 8.7 |
| 3A | 334 | 3.4 | 33.9 | 74.3 | 16.5 | 7.0 |
| 4A | 269 | 3.5 | 36.8 | 74.7 | 14.7 | 8.3 |

The results in TABLE 2 demonstrate again that catalyst activity substantially increases over more than a week after putting the catalyst on stream. Otherwise benzene conversion at 3.4-3.5/hour is about the same after about 300 hours on stream as the values obtained after high-temperature dry activation (38% at 315 hours TOS after high-temperature activation in RN-2A vs. 37-39% at 269-334 hours TOS after low-temperature activation in RN-3A and RN-4A). Note that product selectivity was also essentially the same after low- and high-temperature dry activation at the same catalyst age.

Example 3 (Comparative): Example 1 of WO2012/050751A1

0.7 g catalyst was activated at ambient pressure by ramping the catalyst at 60° C./hour to 145° C. under a flow of 25 sccm $H_2$ and 47 microliter/min benzene (860/hour $H_2$ GHSV, 3.5/hour benzene WHSV, 1.97 mol/mol $H_2$/benzene). Note that the $H_2$/benzene ratio is below 3.0, the stoichiometric ratio for benzene saturation. Such conditions may lead to complete $H_2$ depletion, which in turn can limit catalyst activation and can cause catalyst deactivation by coking.

The catalyst was put on hydroalkylation stream at 145 psig (1000 kPa gauge pressure; 1101 kPa absolute pressure) total pressure, 145° C., feeding 25 sccm (standard cubic centimeters) $H_2$ and 47 microliter/min benzene (860/hour $H_2$ GHSV, 3.5/hour benzene WHSV, 1.97 mol/mol $H_2$/benzene). Benzene conversion lined out at 20% at around 50 hours on stream and was about the same at about 170 hours on stream. CHB selectivity was 82%. In this comparative example, the CHB selectivity was in fact essentially the same as what is obtained after high-temperature dry catalyst activation, and the benzene conversion was merely about half of those of comparative Examples 1 and 2 (37-39% at comparable (3.5/hour) benzene space velocity). Thus, although the catalyst activation procedure disclosed WO2012/050751 does yield some hydroalkylation activity, it is substantially below what the dry hydroalkylation catalyst activation methods yield.

Example 4 (Inventive): 145° C. Activation Using a Condensable Agent

Two experiments were performed to test the efficiency of activation using benzene as a condensable agent according to the present disclosure at 145° C. The catalysts were activated by feeding a 4 mol/mol $H_2$/benzene blend at 1211/hour-1224/hour $H_2$ GHSV and 2.5/hour WHSV at 165 psig total pressure (1138 kPa gauge pressure; 1239 kPa absolute pressure). The bed temperatures were raised at nominally 5° C./hour to 145° C. and were held at 145° C. for 2 hours. After the activation process was completed, the reactors were put on benzene hydroalkylation stream. The results are summarized in TABLE 3.

TABLE 3

Performance of catalyst after 145° C. (low-temperature) activation using benzene as a condensable agent

| Run # RN- | TOS (hour) | WHSV (1/hour) | Benzene Conversion (%) | CHB (%) | C18 (%) | Chex (%) |
|---|---|---|---|---|---|---|
| 5A | 21 | 3.4 | 31.0 | 79.2 | 9.3 | 9.4 |
| 6B | 21 | 2.5 | 46.4 | 75.8 | 12.4 | 9.6 |
| 5A | 278 | 3.4 | 40.9 | 74.9 | 15.5 | 7.4 |
| 6B | 299 | 3.4 | 39.0 | 77.7 | 13.9 | 6.1 |
| 6B | 371 | 3.4 | 41.2 | 76.4 | 15.1 | 6.2 |

The results show that the currently disclosed hydroalkylation catalyst activation method yields high benzene conversion (high catalyst activity) matching or exceeding the best of what was achieved in the comparative examples even though the activation temperature was quite low, 145° C. Later examples will demonstrate that the currently disclosed activation method can deliver even better catalyst performance outperforming any earlier disclosed activation methods when the activation temperature is increased to 190-240° C. Importantly, the results in TABLE 3 reveal that the currently disclosed catalyst activation method yields significantly improved catalyst performance over the comparative activation method in Example 3 above. Without being bound by any theory, it is believed that the improved catalyst performance is due to the higher than stoichiometric 3 mol/mol $H_2$/benzene ratio during activation, which resulted in much less coking.

Example 5 (Inventive): 200° C. Activation Using a Condensable Agent

The catalyst was activated by feeding a 4 mol/mol $H_2$/benzene blend at 1224/hour $H_2$ GHSV and 2.5/hour WHSV at 165 psig total pressure (1138 kPa gauge pressure; 1239 kPa absolute pressure). The bed temperature was raised at nominally 5° C./hour to 200° C. and was held at 200° C. for about 2 hours. After the activation process was completed, the reactor was cooled to 145° C. and put on benzene hydroalkylation stream. The results are summarized in TABLE 4.

TABLE 4

Performance of Catalyst after 200° C. (low-temperature) activation in the presence of benzene as a condensable agent

| Run # RN- | TOS (hour) | Benzene WHSV (1/hour) | Benzene Conversion (%) | Product Selectivity | | |
|---|---|---|---|---|---|---|
| | | | | CHB (%) | C18 (%) | Chex (%) |
| 3B | 47 | 3.4 | 33.2 | 80.2 | 11.2 | 6.4 |
| 3B | 277 | 3.4 | 40.5 | 76.1 | 15.8 | 5.7 |
| 3B | 399 | 3.4 | 43.0 | 74.8 | 17.7 | 5.6 |

The results show that raising the temperature in the activation method according to the present disclosure from 145 to 190° C. somewhat improves catalyst activity and CHB selectivity thus could be advantageous. More importantly, all embodiments of the currently disclosed catalyst activation method are superior (and to a significant degree) to the prior art activation method disclosed in WO2012/050751A1.

Example 6 (Inventive): 240° C. Activation Using Benzene as a Condensable Agent

Two experiments were performed to test the efficiency of activation methods according to the present disclosure at 240° C. The catalysts were activated by feeding a 4 mol/mol $H_2$/benzene blend at 1224/hour $H_2$ GHSV and 2.5/hour WHSV at 165 psig total pressure (1138 kPa gauge pressure; 1239 kPa absolute pressure). The bed temperatures were raised at 5° C./hour to 240° C. and were held at nominally 240° C. for about 2 hours. After the activation process was completed, the reactors were cooled to 145° C. and put on benzene hydroalkylation stream. In one of the two runs, RN-7A, the catalyst was rejuvenated after 246 hours on stream in 50 psig (345 kPa gauge pressure; 446 kPa absolute pressure) flowing $H_2$ at 300° C. The rejuvenation was carried out the same way as described in Example 1 above. The results are summarized in TABLE 5.

TABLE 5

Performance of Catalyst after 240° C. (low-temperature) activation using benzene as a condensable agent

| Run# RN- | TOS (hour) | Benzene WHSV (1/hour) | Benzene Conversion (%) | Product Selectivity | | |
|---|---|---|---|---|---|---|
| | | | | CHB (%) | C18 (%) | Chex (%) |
| 7A | 12 | 2.5 | 56.7 | 74.6 | 15.6 | 7.6 |
| 7B | 12 | 2.5 | 54.0 | 76.0 | 14.7 | 7.1 |
| 7A | 246 | 3.4 | 52.4 | 72.5 | 18.0 | 7.1 |
| 7B | 245 | 3.4 | 48.7 | 73.8 | 17.1 | 6.7 |
| 7A | 390 | 4.9 | 39.8 | 72.7 | 17.4 | 7.2 |
| 7B | 413 | 4.9 | 36.0 | 75.5 | 16.0 | 6.1 |

The results demonstrate that catalyst activity is far superior to what was achieved by any of the comparative activation methods as evidenced by the 49%-52% benzene conversion at 3.4/hour benzene WHSV (see results at around 250 hours on stream in TABLE 5). The comparative dry low-temperature (240° C.) and high-temperature (300° C.) activation methods yielded 37-39% benzene conversions at 3.4-3.5/hour benzene WHSV. Similar (36%) conversion was now achieved at 4.9/hour benzene WHSV with the presently disclosed activation method, which represents an about 40% throughput increase at otherwise identical conditions. The comparison of the present disclosure results with those obtained by the method described in WO2012/050751A1 is even more favorable, since the latter only yielded 20% benzene conversion at 3.5/hour benzene WHSV. Interestingly, while catalytic activity is substantially increased by the currently disclosed activation method, CHB selectivity remained essentially unchanged if compared properly at the same reactor conditions, including benzene conversion. At 36-38% benzene conversion, the catalyst activated by the comparative high-temperature and low-temperature dry methods gave 75.7% and 74.7% CHB, respectively. That is the same within experimental scatter as the 75.5% obtained in RN-7B (see results at 413 hours on stream).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A hydroalkylation process, the process comprising:
(I) providing a catalyst precursor comprising a solid acid and a hydrogenation metal;
(II) treating the catalyst precursor under activation conditions in the presence of hydrogen and a condensable agent comprising a hydrocarbon compound to produce an activated catalyst, wherein the molar ratio of hydrogen to the condensable agent is at least 3.0; and subsequently
(III) contacting the activated catalyst with a first aromatic compound and hydrogen under hydroalkylation conditions to produce a hydroalkylation product comprising a alkylated aromatic compound.

E2. The process of E1, wherein in step (II), at least a part of the condensable agent is in liquid state.

E3. The process of E1 or E2, wherein the hydrocarbon compound in the condensable agent has a structure represented by the following formula (F-I):

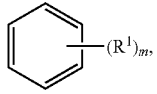

(F-I)

where:

$R^1$, the same or different at each occurrence, each independently represents a substituted or unsubstituted linear, branched acyclic, or cyclic alkyl or alkenyl group having from 1 to 20 carbon atoms; and m is an integer from 0 to 5; preferably 0 or 1.

E4. The process of any of E1 to E3, wherein the condensable agent comprises the first aromatic compound.

E5. The process of any of E1 to E4, wherein in step (II), the activation conditions comprise a temperature in a range from 120° C. to 350° C.

E6. The process of E5, wherein step (II) comprises treating the catalyst precursor at a temperature in a range from 130° C. to 250° C. for a period in a range from 0.5 hour to 48 hours.

E7. The process of E5, wherein step (II) comprises treating the catalyst precursor in the range from Tmax−20° C. to Tmax for a period in a range from 0.5 hour to 48 hours, where Tmax is the highest temperature the catalyst precursor is subjected to in step (II).

E8. The process of E7, wherein Tmax is in a range from 140° C. to 250° C.

E9. The process of any of E1 to E8, wherein the molar ratio of hydrogen to the condensable agent in step (II) is at least 4.0.

E10. The process of any of E1 to E9, wherein the molar ratio of hydrogen to the first aromatic compound in step (III) is in a range from 0.1 to 1.9.

E11. The process of any of E1 to E10, wherein the first aromatic compound has a structure represented by the following formula (F-II):

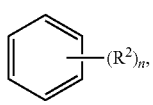

(F-II)

where:

$R^2$, the same or different at each occurrence, each independently represents a substituted or unsubstituted linear, branched acyclic, or cyclic alkyl or alkenyl group having from 1 to 20 carbon atoms; and n is an integer from 0 to 5, preferably 0 or 1.

E12. The process of E11, wherein the first aromatic compound is selected from benzene, toluene, ethylbenzene, n-propylbenzene, cumene, n-butylbenzene, 2-phenylbutane, o-xylene, m-xylene, p-xylene, and mixtures thereof.

E13. The process of E11 or E12, wherein the alkylated aromatic compound has a structure represented by the following formula (F-III):

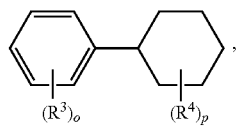

(F-III)

where:

$R^3$ and $R^4$, the same or different at each occurrence, each independently represents a substituted or unsubstituted linear, branched acyclic, or cyclic alkyl or alkenyl having from 1 to 20 carbon atoms; and o and p are independently integers from 0 to 5. Preferably o and p are independently 0 or 1.

E14. The process of E13, wherein the alkylated aromatic compound is selected from:
cyclohexylbenzene;
dicyclohexylbenzene;
tricyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene; and
methylethylcyclohexyl-methylethylbenzene.

E15. The process of E14, wherein the alkylated aromatic compound is cyclohexylbenzene, and the first aromatic compound is benzene.

E16. The process of any of E1 to E15, wherein between steps (II) and (III), the activated catalyst is not subjected to contacting with an atmosphere comprising at least 95% by mole of hydrogen at temperatures higher than 120° C. for a duration longer than 30 minutes.

E17. The process of any of E1 to E16, wherein in step (I), at least 90% by mole of the hydrogenation metal has an oxidation state of higher than zero.

E18. The process of any of E1 to E17, wherein in step (I), the solid acid comprises a molecular sieve.

E19. The process of E18, wherein the molecular sieve is of MCM-22 type.

E20. The process of any of E1 to E19, wherein the hydrogenation metal in the catalyst precursor comprises at least one of Re, Ru, Os, Rh, Ir, Ni, Pd, and Pt.

E21. The process of any of E1 to E20, wherein the catalyst precursor comprises an inorganic oxide support component.

E22. The process of E21, wherein the inorganic oxide support component comprises at least one of alumina, silica, zirconia, and titania.

E23. The process of any of E1 to E22, wherein the contacting step (III) is conducted at a temperature in a range from 90° C. to 180° C., and a pressure in a range from 100 kPa to 5000 kPa.

E24. The hydroalkylation process of any of E1 to E23, wherein in the contacting step (III), at least a portion of the first aromatic compound is in liquid phase.

E25. The hydroalkylation process of any of E1 to E24, wherein the contacting step (III) is conducted at a space velocity of 0.5 to 15.0 grams of the first aromatic compound per gram of the activated catalyst per hour.

E26. A process for making phenol and/or cyclohexanone, the process comprising:
(A) producing cyclohexylbenzene by:
(AI) supplying hydrogen and benzene into a hydroalkylation reactor;

(AII) contacting the hydrogen and benzene with a hydroalkylation catalyst produced by a process according to any of the preceding claims;

(B) oxidizing at least a portion of the cyclohexylbenzene to obtain an oxidation product comprising cyclohexylbenzene hydroperoxide; and (C) subjecting at least a portion of the cyclohexylbenzene hydroperoxide in the oxidation product to cleavage to obtain a cleavage product comprising phenol and cyclohexanone.

The invention claimed is:

1. A hydroalkylation process, the process comprising:

(I) providing a catalyst precursor comprising a solid acid and a hydrogenation metal;

(II) treating the catalyst precursor under activation conditions in the presence of hydrogen and a condensable agent comprising a hydrocarbon compound to produce an activated catalyst, wherein the molar ratio of hydrogen to the condensable agent is at least 3.0, wherein the activation conditions comprise treating the catalyst precursor at a temperature in a range from 130° C. to 250° C. for a period in a range from 0.5 hour to 48 hours; and subsequently (III) contacting the activated catalyst with a first aromatic compound and hydrogen under hydroalkylation conditions to produce a hydroalkylation product comprising an alkylated aromatic compound.

2. The process of claim 1, wherein in step (II), at least a part of the condensable agent is in liquid state.

3. The process of claim 1, wherein the hydrocarbon compound in the condensable agent has a structure represented by the following formula (F-I):

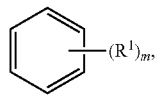

(F-I)

where:

$R^1$, the same or different at each occurrence, each independently represents a substituted or unsubstituted linear, branched acyclic, or cyclic alkyl or alkenyl group having from 1 to 20 carbon atoms; and m is an integer from 0 to 5.

4. The process of claim 1, wherein the condensable agent comprises the first aromatic compound.

5. The process of claim 1, wherein step (II) comprises treating the catalyst precursor at a temperature in the range from Tmax−20° C. to Tmax for a period in a range from 0.5 hour to 48 hours, where Tmax is the highest temperature the catalyst precursor is subjected to in step (II).

6. The process of claim 5, wherein Tmax is in a range from 140° C. to 250° C.

7. The process of claim 1, wherein the molar ratio of hydrogen to the condensable agent in step (II) is at least 4.0.

8. The process of claim 1, wherein the molar ratio of hydrogen to the first aromatic compound in step (III) is in a range from 0.1 to 0.9.

9. The process of claim 1, wherein the first aromatic compound has a structure represented by the following formula (F-II):

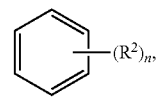

(F-II)

where:

$R^2$, the same or different at each occurrence, each independently represents a substituted or unsubstituted linear, branched acyclic, or cyclic alkyl or alkenyl group having from 1 to 20 carbon atoms; and n is an integer from 1 to 5.

10. The process of claim 9, wherein the first aromatic compound is selected from benzene, toluene, ethylbenzene, n-propylbenzene, cumene, n-butylbenzene, 2-phenylbutane, o-xylene, m-xylene, p-xylene, and mixtures thereof.

11. The process of claim 9, wherein the alkylated aromatic compound has a structure represented by the following formula (F-III):

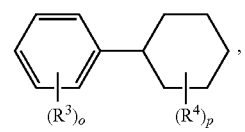

(F-III)

where:

$R^3$ and $R^4$, the same or different at each occurrence, each independently represents a substituted or unsubstituted linear, branched acyclic, or cyclic alkyl or alkenyl having from 1 to 20 carbon atoms; and o and p are independently integers from 0 to 5.

12. The process of claim 11, wherein the alkylated aromatic compound is selected from:
cyclohexylbenzene;
dicyclohexylbenzene;
tricyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene; and
methylethylcyclohexyl-methylethylbenzene.

13. The process of claim 11, wherein the alkylated aromatic compound is cyclohexylbenzene, and the first aromatic compound is benzene.

14. The process of claim 1, wherein in step (I), the solid acid comprises a molecular sieve.

15. The process of claim 14, wherein the molecular sieve is of MCM-22 type.

16. The process of claim 1, wherein the hydrogenation metal in the catalyst precursor comprises at least one of Re, Ru, Os, Rh, Ir, Ni, Pd, and Pt.

17. The process of claim 1, wherein the catalyst precursor comprises an inorganic oxide support component.

18. The process of claim 17, wherein the inorganic oxide support component comprises at least one of alumina, silica, zirconia, and titania.

19. The process of claim 1, wherein the contacting step (III) is conducted at a temperature in a range from 90° C. to 180° C., and a pressure in a range from 100 kPa to 5000 kPa.

20. The process of claim 1, wherein in the contacting step (III), at least a portion of the first aromatic compound is in liquid phase.

21. The process of claim 1, wherein the contacting step (III) is conducted at a space velocity of 0.5 to 15.0 grams of the first aromatic compound per gram of the activated catalyst per hour.

22. A process for making phenol and/or cyclohexanone, the process comprising:
 (A) producing cyclohexylbenzene by:
  (AI) supplying hydrogen and benzene into a hydroalkylation reactor;
  (AII) contacting the hydrogen and benzene with a hydroalkylation catalyst produced by a process according to claim 1;
 (B) oxidizing at least a portion of the cyclohexylbenzene to obtain an oxidation product comprising cyclohexylbenzene hydroperoxide; and
 (C) subjecting at least a portion of the cyclohexylbenzene hydroperoxide in the oxidation product to cleavage to obtain a cleavage product comprising phenol and cyclohexanone.

* * * * *